(12) United States Patent
Basch et al.

(10) Patent No.: US 8,158,394 B2
(45) Date of Patent: Apr. 17, 2012

(54) GENETICALLY STABLE PLASMID EXPRESSING PDH AND FDH ENZYMES

(75) Inventors: Jonathan Basch, DeWitt, NY (US); Thomas Franceschini, Cicero, NY (US); Suo Win Liu, Longmont, CO (US); Shu-Jen Chiang, Manlius, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 188 days.

(21) Appl. No.: 12/756,700

(22) Filed: Apr. 8, 2010

(65) Prior Publication Data

US 2010/0261236 A1    Oct. 14, 2010

Related U.S. Application Data

(60) Provisional application No. 61/167,676, filed on Apr. 8, 2009.

(51) Int. Cl.
 *C12P 17/06* (2006.01)
 *C12N 9/02* (2006.01)
 *C12N 1/20* (2006.01)
 *C12N 15/00* (2006.01)
 *C07H 21/04* (2006.01)

(52) U.S. Cl. .............. 435/135; 435/189; 435/252.3; 435/320.1; 536/23.2

(58) Field of Classification Search .............. 435/135, 435/189, 252.3, 320.1; 536/23.2
See application file for complete search history.

(56) References Cited

U.S. PATENT DOCUMENTS

| 6,068,991 | A | 5/2000 | Liu et al. |
| 6,395,767 | B2 | 5/2002 | Robl et al. |
| 7,420,079 | B2 | 9/2008 | Vu et al. |

FOREIGN PATENT DOCUMENTS

| EP | 1918375 | 5/2008 |
| WO | 2005106011 A2 | 11/2005 |

OTHER PUBLICATIONS

Hanson et al., "Synthesis of allysine ethylene acetal using phenylalanine dehydrogenase from Thermoactinomyces intermedius," 26 (1) Enzyme and Microbial Technology 348-58 (2000).
Patel, "Microbial/enzymatic synthesis of chiral drug intermediates," 47 Advances in Applied Microbiology 33-78 (2000).
International Search Report, Jun. 30, 2006.
Hanessian, et al, "Probing the Importance of Spacial and Conformational Domains in Captopril Analogs for Angiotensin Converting Enzyme Activity", Bioorganic & Med. Chem. Lett., (8), 2123-2128 (1998).
Imashiro and Kuroda, "Asymmetric synthesis of methyl (2R,3S)-3-(4-methoxyphenyl) glycidate, a key intermediate of diltiazem, via Mukalyama aldol reaction." Tetra. Lett. (42), 1313-1315 (2001).
Reetz, et al. "General Synthesis of Potentially Antiviral alpha-Adamantyl Carbonyl Compounds.", Angew. Chem. Int. Ed. Engl. (18), No. 1 (1979).
Sagnard, et al. "Enantioselective Synthesis of Cyclopropane alpha-Amino Acids: Synthesis of N-Boc-cis-(2S, 3R, 4S)-3,4-Methanoproline and N-Boc-(2S,3R,4S)-3,4-Methanoglutamic Acid." Tetra. Lett., vol. 36, No. 18, 3149-3152 (1995).
Tverezovsky, et al., "Synthesis of (2S,3R,4S)-3,4-Methanoproline and Analogues by Cyclopropylidene Insertion." Tetrahedron, vol. 53, No. 43, 14773-14792 (1997).
Galkin, et al. "Synthesis of Optically Active Amino Acids from alpha-Keto Acids with *Escherichia coli* Cells Expressing Heterologous Genes." Appl. and Env. Microbiol., 4651-4656 (Dec. 1997).
Kimura, et al. "Two-Cistronic Expression Plasmids for High-Level Gene Expression in *Escherichia coli* Preventing Translational Inhibition Caused by the Inhibition Caused by the Intramolecular Local Secondary Structure of mRNA.", J. Biochem., 137, 523-533 (2006).

*Primary Examiner* — Tekchand Saidha
(74) *Attorney, Agent, or Firm* — McDonnell Boehnen Hulbert & Berghoff

(57) ABSTRACT

Bi-cistronic plasmids used for the expression of formate dehydrogenase (FDH) and modified phenylalanine dehydrogenase (PDHmod) are provided.

9 Claims, 5 Drawing Sheets

Figure 2(a)

```
aagcttactc cccatccccc tgttgacaat taatcatcgg ctcgtataat gtgtggaatt   60
gtgagcggat aacaatttca cacaggaaac aggatctcca tggatattcg tccattgcat  120
gatcgcgtga tcgtcaagcg taaagaagtt gaaactaaat ctgctggcgg catcgttctg  180
accggctctg cagcggctaa atccaccegc ggcgaagtgc tggctgtcgg caatggccgt  240
atccttgaaa atggcgaagt gaagccgctg gatgtgaaag ttggcgacat cgttattttc  300
aacgatggct acggtgtgaa atctgagaag atcgacaatg aagaagtgtt gatcatgtcc  360
gaaagcgaca ttctggcaat tgttgaagcg taatccgcgc acgacactga acatacgaat  420
ttaaggaata aagatcatga aatcgttct cgttttgtac tccgctggta agcacgccgc  480
cgatgaacca aagttgtatg gttgtatcga aatgaattg ggtattagac aatggcttga  540
gaagggcggc catgaattgg ttactacatc agacaaagag ggtgaaaact ctgagttaga  600
aaagcacatt cctgacgctg atgtgattat ttccactcca ttccatccag cctacatcac  660
gaaggagaga atccaaaaag ccaagaagct gaagttgttg gtcgttgctg gtgtcggttc  720
cgaccacatt gacttggact acattgaaca aaatggccta gatatttcgg tcctagaggt  780
tactggttcc aacgttgttt cagtggctga gcatgtcgtt atgactatat tgaacttggt  840
gagaaacttt gttccagctc acgagcaaat tgttaaccac ggctgggacg ttgctgccat  900
cgccaaggac gcctacgata tcgaaggtaa gaccatcgca acaattggtg ctggaagaat  960
tggttacaga gtcttagaga gacttgtggc tttcaaccct aaggaattgt tgtactacga 1020
ctaccaaggt cttccaaaag aggccgagga aaaagttggt gccagaagag tcgacactgt 1080
cgaggagctg gttgctcaag ccgatgttgt taccgtcaat gccccactgc acgcaggtac 1140
taagggttta gttaacaagg agcttctgtc caagttcaag aagggtgctt ggttggttaa 1200
cacagccaga ggtgccatct gcaatgctca agatgtcgct gatgccgttg catctggtca 1260
attgagaggt tacggtggtg acgtctggtt ccctcagcca gctccaaagg accatccatg 1320
gagagatatg agaaacaagt acggatacgg aaacgccatg actcctcatt actcaggtac 1380
cactttggac gcccaggtca gatatgccga aggtaccaag aacatcttga actcattcct 1440
taccaagaag tttgactaca gacctcaaga tgtcattctt ttgaacggta agtacaagac 1500
caaggcttat ggtaatgaca aaaaggtcgc ataaggatct gcgcacgaca ctgaacatac 1560
gaatttaagg aataaacata tgcgcgacgt gtttgaaatg atggaccgct atggccacga 1620
gcaggtcatt ttttgccgtc atccgcaaac cggtctcaaa gcgatcatcg ccttgcataa 1680
tacaaccgcg gggccggctt tgggtggatg ccgcatgatc ccgtatgctt cgacggacga 1740
agccttggag gatgttttgc ggttgtccaa aggcatgacc tataaatgca gtctggcgga 1800
tgtggacttt ggcggggggaa aaatggttat catcggcgat ccgaaaaaag ataaatcgcc 1860
ggagttgttt cgcgtgatcg gccgttttgt gggcgggtta acggccgtt tctataccgg 1920
aaccgacatg ggaaccaatc cggaagattt tgtccatgcc gccagggaat cgaaatcttt 1980
tgccggattg ccgacatcgt acggcggaag cggggacaca tccattccca ccgcgctcgg 2040
ggtgtttcac ggaatgcggg ccaccgcccg gttttatgg gggacggatc agctgaaagg 2100
gcgtgtggtt gccatccaag gagtcggcaa ggtgggagag cgcttgttgc agcttttggt 2160
cgaagtgggg gcttactgca aaattgccga catcgattcg gtgcgatgcg aacagctgaa 2220
agaaaagtat ggcgacaagg tccaattggt ggatgtgaac cggattcaca aggagagttg 2280
cgatattttc tcgccttgcg ccaaaggcgg cgtggtcaat gatgacacca ttgacgagtt 2340
ccgttgcctg gccattgtcg gatccgccaa caaccaactg gtggaagacc ggcatgggc 2400
actgcttcaa aaacggagca tttggtatgc acccgattat ctggtgaatg ccggcgggct 2460
gattcaagtg gctgatgaac tggaaggctt ccatgaagag agagtgctcg ccaaaaccga 2520
agcgatttat gacatggtcc tggatatttt tcaccgggcg aaaaatgaga atattaccac 2580
ttgtgaggca gcggaccgga tcgtgatgga gcgtttgaaa aagttaaccg atattcgccg 2640
gatcttgttg gaggatcccc gcaacagcgc ggagggtac ctcgagccgc ggcggccgcg 2700
aattaattcg ccttagacat gactgttcct cagttcaagt tgggcactta cgagaagacc 2760
ggtcttgcta gcccggggt ggcgaagaac tccagcatga atccccgcg ctggaggatc 2820
atccagccgg cgtcccggaa aacgattccg aagcccaacc tttcatagaa ggcggcggtg 2880
gaatcgaaat ctcgtgatgg caggttgggc gtcgcttggt cggtcattc gaaccccaga 2940
gtcccgctca gaagaactcg tcaagaaggc gatagaaggc gatgcgctgc gaatcgggag 3000
cggcgatacc gtaaagcacg aggaagcggt cagcccattc gccgccaagc tcttcagcaa 3060
tatcacgggt agccaacgct atgtcctgat agcggtccgc cacacccagc cggccacagt 3120
cgatgaatcc agaaaagcgg ccattttcca ccatgatatt cggcaagcag gcatcgccgt 3180
gggtcacgac gagatcctcg ccgtcgggca tgcgcgcctt gagcctggcg aacagttcgg 3240
```

Figure 2(b)

```
ctggcgcgag cccctgatgc tcttcgtcca gatcatcctg atcgacaaga ccggcttcca 3300
tccgagtacg tgctcgctcg atgcgatgtt tcgcttggtg gtcgaatggg caggtagccg 3360
gatcaagcgt atgcagccgc cgcattgcat cagccatgat ggatactttc tcggcaggag 3420
caaggtgaga tgacaggaga tcctgccccg gcacttcgcc caatagcagc cagtcccttc 3480
ccgcttcagt gacaacgtcg agcacagctg cgcaaggaac gcccgtcgtg gccagccacg 3540
atagccgcgc tgcctcgtcc tgcagttcat tcagggcacc ggacaggtcg gtcttgacaa 3600
aaagaaccgg gcgcccctgc gctgacagcc ggaacacggc ggcatcagag cagccgattg 3660
tctgttgtgc ccagtcatag ccgaatagcc ctccaccca agcggccgga gaacctgcgt 3720
gcaatccatc ttgttcaatc atgcgaaacg atcctcatcc tgtctcttga tcagatcttg 3780
atccctgcg ccatcagatc cttggcggca agaaagccat ccagtttact ttgcagggtt 3840
cccaaccttta ccagagggcg ccccagctgg caattccggt tcgcttgctg tccataaaac 3900
cgcccagtct agctatcgcc atgtaagccc actgcaagct acctgctttc tctttgcgct 3960
tgcgttttcc cttgtccaga tagcccagta gctgacattc atccggggtc agcaccgttt 4020
ctgcggactg gctttctacg tgttccgctt cctttagcag cccttgcgcc ctgagtgctt 4080
gcggcagcgt gaagctagct tggcaatggc aacaacgttg cgcaaactat taactggcga 4140
actacttact ctagcttccc ggcaacaatt aatagactgg atggaggcgg ataaagttgc 4200
aggaccactt ctgcgctcgg cccttccggc tggctggttt attgctgata atctggagc 4260
cggtgagcgt gggtctcgcg gtatcattgc agcactgggg ccagatggta agccctcccg 4320
tatcgtagtt atctacacga cggggagtca ggcaactatg gatgaacgaa atagacagat 4380
cgctgagata ggtgcctcac tgattaagca ttggtaactg tcagaccaag tttactcata 4440
tatactttag attgatttaa aacttcattt ttaatttaaa aggatctagg tgaagatcct 4500
ttttgataat ctcatgcatg accaaaatcc cttaacgtga gttttcgttc cactgagcgt 4560
cagaccccgt agaaaagatc aaaggatctt cttgagatcc ttttttttctg cgcgtaatct 4620
gctgcttgca aacaaaaaaa ccaccgctac cagcggtggt ttgtttgccg gatcaagaga 4680
taccaactct ttttccgaag gtaactggct tcagcagagc gcagatacca atactgtcc 4740
ttctagtgta gccgtagtta ggccaccact tcaagaactc tgtagcaccg cctacatacc 4800
tcgctctgct aatcctgtta ccagtggctg ctgccagtgg cgataagtcg tgtcttaccg 4860
ggtggactca agacgatagt taccggataa ggcgcagcgg tcgggctgaa cggggggttc 4920
gtgcacacag cccagcttgg agcgaacgac ctacaccgaa ctgagatacc taacagcgtg 4980
agctatgaga aagcgccacg cttcccgaag ggagaaaggc ggacaggtat ccggtaagcg 5040
gcagggtcgg aacaggagag cgcacgaggg agcttccagg gggaaacgcc tggtatcttt 5100
atagtcctgt cgggtttcgc cacctctgac ttgagcgtcg attttttgtga tgctcgtcag 5160
gggggcggag cctatggaaa aacgccagca acgcggcctt tttacggttc ctggccttt 5220
gctggccttt tgctcacatg ttctttcctg cgttatcccc tgattctgtg ataaccgta 5280
ttaccgcctt tgagtgagct gataccgctc gccgcagccg aacgaccgag cgcagcgagt 5340
cagtgagcga ggaagcggaa gagcgcctga tgcggtattt tctccttacg catctgtgcg 5400
gtatttcaca ccgcatagga attcgctaga gtcggaagca taaagtgta aagcctgggg 5460
tgcctaatga gtgagctaac tcacatttaa ttgcgttgcg ctcactgccc gctttccagt 5520
cgggaaacct gtcgtgccag ctgcattaat gaatcggcca acgcgcgggg agaggcggtt 5580
tgcgtattgg cgccagggt ggttttttctt tcaccagtg agacgggcaa cagctgattg 5640
cccttcaccg cctggccctg agagagttgc agcaagcggt ccacgctggt ttgccccagc 5700
aggcgaaaat cctgtttgat ggtggttgac ggcgggatat aacatgagct gtcttcggta 5760
tcgtcgtatc ccactaccga gatatccgca ccaacgcgca gcccggactc ggtaatggcg 5820
cgcattgcgc ccagcgccat ctgatcgttg gcaaccagca tcgcagtggg aacgatgccc 5880
tcattcagca tttgcatggt ttgttgaaaa ccggacatgg cactccagtc gccttcccgt 5940
tccgctatcg gctgaatttg attgcgagtg agatatttat gccagccagc cagacgcaga 6000
cgcgccgaga cagaacttaa tgggcccgct aacagcgcga tttgctggtg acccaatgcg 6060
accagatgct ccacgcccag tcgcgtaccg tcttcatggg agaaaataat actgttgatg 6120
ggtgtctggt cagagacatc aagaaataac gccggaacat tagtgcaggc agcttccaca 6180
gcaatggcat cctggtcatc cagcggatag ttaatgatca gcccactgac gcgttgcgcg 6240
agaagattgt gcaccgccgc tttacaggct tcgacgccgc ttcgttctac catcgacacc 6300
accacgctgg cacccagttg atcggcgcga gatttaatcg ccgcgacaat ttgcgacggc 6360
gcgtgcaggg ccagactgga ggtggcaacg ccaatcagca acgactgttt gcccgccagt 6420
tgttgtgcca cgcggttggg aatgtaattc agctccgcca tcgccgcttc cacttttttcc 6480
```

Figure 2(c)

```
cgcgttttcg cggaaacgtg gctggcctgg ttcaccacgc gggaaacggt ctgataagag   6540
acaccggcat actctgcgac atcgtataac gttactggtt tcacattcac caccctgaat   6600
tgactctctt ccgggcgcta tcatgccata ccgcgaaagg ttttgcgcca ttcgatggtg   6660
tcggcatgc  (SEQ ID NO: 2)                                            6669
```

| Lane | Sample |
|---|---|
| 1 | 1Kb Plus Molecular Weight Marker |
| 2 | JM110 Plasmid DNA EcoRI digested |

SEQUENCE LISTING

```
<160> NUMBER OF SEQ ID NOS: 9

<210> SEQ ID NO 1
<211> LENGTH: 2280
<212> TYPE: DNA
<213> ORGANISM: Artificial Sequence
<220> FEATURE:
<223> OTHER INFORMATION: Synthetic

<400> SEQUENCE: 1
atgaaaatcg ttctcgtttt gtactccgct ggtaagcacg ccgccgatga accaaagttg      60
tatggttgta tcgaaaatga attgggtatt agacaatggc ttgagaaggg cggccatgaa     120
ttggttacta catcagacaa agagggtgaa aactctgagt tagaaaagca cattcctgac     180
gctgatgtga ttatttccac tccattccat ccagcctaca tcacgaagga gagaatccaa     240
aaagccaaga agctgaagtt gttggtcgtt gctggtgtcg gttccgacca cattgacttg     300
gactacattg aacaaaatgg cctagatatt tcggtcctag aggttactgg ttccaacgtt     360
gtttcagtgg ctgagcatgt cgttatgact atattgaact tggtgagaaa ctttgttcca     420
gctcacgagc aaattgttaa ccacggctgg gacgttgctc ccatcgccaa ggacgcctac     480
gatatcgaag gtaagaccat cgcaacaatt ggtgctggaa gaattggtta cagagtctta     540
```

-continued

```
gagagacttg tggctttcaa ccctaaggaa ttgttgtact acgactacca aggtcttcca      600
aaagaggccg aggaaaaagt tggtgccaga agagtcgaca ctgtcgagga gctggttgct      660
caagccgatg ttgttaccgt caatgcccca ctgcacgcag gtactaaggg tttagttaac      720
aaggagcttc tgtccaagtt caagaagggt gcttggttgg ttaacacagc cagaggtgcc      780
atctgcaatg ctcaagatgt cgctgatgcc gttgcatctg gtcaattgag aggttacggt      840
ggtgacgtct ggttccctca gccagctcca aaggaccatc catggagaga tatgagaaac      900
aagtacggat acggaaacgc catgactcct cattactcag gtaccacttt ggacgcccag      960
gtcagatatg ccgaaggtac caagaacatc ttgaactcat tccttaccaa gaagtttgac     1020
tacagacctc aagatgtcat tcttttgaac ggtaagtaca agaccaaggc ttatggtaat     1080
gacaaaaagg tcgcataagg atctgcgcac gacactgaac atacgaattt aaggaataaa     1140
catatgcgcg acgtgtttga atgatggac cgctatggcc acgagcaggt cattttttgc      1200
cgtcatccgc aaaccggtct caaagcgatc atcgccttgc ataatacaac cgcggggccg     1260
gcttttgggtg atgccgcat gatcccgtat gcttcgacgg acgaagcctt ggaggatgtt     1320
ttgcggttgt ccaaaggcat gacctataaa tgcagtctgg cggatgtgga ctttggcggg     1380
ggaaaaatgg ttatcatcgg cgatccgaaa aagataaat cgccggagtt gtttcgcgtg      1440
atcggccgtt ttgtgggcgg gttaaacggc cgtttctata ccggaaccga catgggaacc     1500
aatccggaag attttgtcca tgccgccagg gaatcgaaat cttttgccgg attgccgaca     1560
tcgtacggcg aagcgggga cacatccatt cccaccgcgc tcggggtgtt tcacggaatg     1620
cgggccaccg cccggttttt atgggggacg gatcagctga agggcgtgt ggttgccatc      1680
caaggagtcg gcaaggtggg agagcgcttg ttgcagcttt tggtcgaagt gggggcttac     1740
tgcaaaattg ccgacatcga ttcggtgcga tgcgaacagc tgaagaaaa gtatggcgac      1800
aaggtccaat tggtggatgt gaaccggatt cacaaggaga gttgcgatat tttctcgcct     1860
tgcgccaaag gcggcgtggt caatgatgac accattgacg agttccgttg cctggccatt     1920
gtcggatccg ccaacaacca actggtggaa accggcatg gggcactgct tcaaaaacgg      1980
agcatttggt atgcacccga ttatctggtg aatgccggcg ggctgattca agtggctgat     2040
gaactggaag gcttccatga agagagagtg ctcgccaaaa ccgaagcgat ttatgacatg     2100
gtcctggata tttttcaccg gcgaaaaat gagaatatta ccacttgtga ggcagcggac      2160
cggatcgtga tggagcgttt gaaaaagtta accgatattc gccggatctt gttgaggat      2220
ccccgcaaca gcgcggaggg gtacctcgag ccgcggcggc cgcgaattaa ttcgccttag     2280
```

`<210>` SEQ ID NO 2
`<211>` LENGTH: 6669
`<212>` TYPE: DNA
`<213>` ORGANISM: Artificial Sequence
`<220>` FEATURE:
`<223>` OTHER INFORMATION: Synthetic

`<400>` SEQUENCE: 2

```
aagcttactc cccatccccc tgttgacaat taatcatcgg ctcgtataat gtgtggaatt       60
gtgagcggat aacaatttca cacaggaaac aggatctcca tggatattcg tccattgcat      120
gatcgcgtga tcgtcaagcg taagaagtt gaaactaaat ctgctggcgg catcgttctg       180
accggctctg cagcggctaa atccacccgc ggcgaagtgc tggctgtcgg caatggccgt      240
atccttgaaa atggcgaagt gaagccgctg atgtgaaaa ttggcgacat cgttattttc       300
aacgatggct acggtgtgaa atctgagaag atcgacaatg aagaagtgtt gatcatgtcc      360
```

```
gaaagcgaca ttctggcaat tgttgaagcg taatccgcgc acgacactga acatacgaat     420
ttaaggaata aagatcatga aaatcgttct cgttttgtac tccgctggta agcacgccgc     480
cgatgaacca aagttgtatg gttgtatcga aaatgaattg ggtattagac aatggcttga     540
gaagggcggc catgaattgg ttactacatc agacaaagag ggtgaaaact ctgagttaga     600
aaagcacatt cctgacgctg atgtgattat ttccactcca ttccatccag cctacatcac     660
gaaggagaga atccaaaaag ccaagaagct gaagttgttg gtcgttgctg gtgtcggttc     720
cgaccacatt gacttggact acattgaaca aaatggccta gatatttcgg tcctagaggt     780
tactggttcc aacgttgttt cagtggctga gcatgtcgtt atgactatat tgaacttggt     840
gagaaacttt gttccagctc acgagcaaat tgttaaccac ggctgggacg ttgctgccat     900
cgccaaggac gcctacgata tcgaaggtaa gaccatcgca acaattggtg ctggaagaat     960
tggttacaga gtcttagaga gacttgtggc tttcaacccct aaggaattgt tgtactacga     1020
ctaccaaggt cttccaaaag aggccgagga aaaagttggt gccagaagag tcgacactgt     1080
cgaggagctg gttgctcaag ccgatgttgt taccgtcaat gccccactgc acgcaggtac     1140
taagggttta gttaacaagg agcttctgtc caagttcaag aagggtgctt ggttggttaa     1200
cacagccaga ggtgccatct gcaatgctca agatgtcgct gatgccgttg catctggtca     1260
attgagaggt tacggtggtg acgtctggtt ccctcagcca gctccaaagg accatccatg     1320
gagagatatg agaaacaagt acggatacgg aaacgccatg actcctcatt actcaggtac     1380
cactttggac gcccaggtca gatatgccga aggtaccaag aacatcttga actcattcct     1440
taccaagaag tttgactaca gacctcaaga tgtcattctt ttgaacggta agtacaagac     1500
caaggcttat ggtaatgaca aaaaggtcgc ataaggatct gcgcacgaca ctgaacatac     1560
gaatttaagg aataaacata tgcgcgacgt gtttgaaatg atggaccgct atggccacga     1620
gcaggtcatt ttttgccgtc atccgcaaac cggtctcaaa gcgatcatcg ccttgcataa     1680
tacaaccgcg gggccggctt tgggtggatg ccgcatgatc ccgtatgctt cgacggacga     1740
agccttggag gatgttttgc ggttgtccaa aggcatgacc tataaatgca gtctggcgga     1800
tgtggacttt ggcgggggaa aaatggttat catcggcgat ccgaaaaaag ataaatcgcc     1860
ggagttgttt cgcgtgatcg gccgttttgt gggcgggtta acggccgttt tctataccgg     1920
aaccgacatg ggaaccaatc cggaagattt tgtccatgcc gccagggaat cgaaatcttt     1980
tgccggattg ccgacatcgt acggcggaag cggggacaca tccattccca ccgcgctcgg     2040
ggtgtttcac ggaatgcggg ccaccgcccg gtttttatgg gggacggatc agctgaaagg     2100
gcgtgtggtt gccatccaag gagtcggcaa ggtgggagag cgcttgttgc agcttttggt     2160
cgaagtgggg gcttactgca aaattgccga catcgattcg gtgcgatgcg aacagctgaa     2220
agaaaagtat ggcgacaagg tccaattggt ggatgtgaac cggattcaca aggagagttg     2280
cgatattttc tcgccttgcg ccaaaggcgg cgtggtcaat gatgacacca ttgacgagtt     2340
ccgttgcctg gccattgtcg gatccgccaa caaccaactg gtggaagacc ggcatggggc     2400
actgcttcaa aaacggagca tttggtatgc acccgattat ctggtgaatg ccggcgggct     2460
gattcaagtg gctgatgaac tggaaggctt ccatgaagag agagtgctcg ccaaaaccga     2520
agcgatttat gacatggtcc tggatatttt tcaccgggcg aaaaatgaga atattaccac     2580
ttgtgaggca gcggaccgga tcgtgatgga gcgtttgaaa aagttaaccg atattcgccg     2640
gatcttgttg gaggatcccc gcaacagcgc ggagggggtac ctcgagccgc ggcggccgcg     2700
aattaattcg ccttagacat gactgttcct cagttcaagt tgggcactta cgagaagacc     2760
```

```
ggtcttgcta gcccggggtg ggcgaagaac tccagcatga gatccccgcg ctggaggatc    2820
atccagccgg cgtcccggaa aacgattccg aagcccaacc tttcatagaa ggcggcggtg    2880
gaatcgaaat ctcgtgatgg caggttgggc gtcgcttggt cggtcatttc gaacccccaga   2940 gtcccgctca aagaactcg tcaagaaggc gatagaaggc gatgcgctgc gaatcgggag     3000
cggcgatacc gtaaagcacg aggaagcggt cagcccattc gccgccaagc tcttcagcaa    3060
tatcacgggt agccaacgct atgtcctgat agcggtccgc cacacccagc cggccacagt    3120
cgatgaatcc agaaaagcgg ccattttcca ccatgatatt cggcaagcag gcatcgccgt    3180
gggtcacgac gagatcctcg ccgtcgggca tgcgcgcctt gagcctggcg aacagttcgg    3240
ctggcgcgag cccctgatgc tcttcgtcca gatcatcctg atcgacaaga ccggcttcca    3300
tccgagtacg tgctcgctcg atgcgatgtt tcgcttggtg gtcgaatggg caggtagccg    3360
gatcaagcgt atgcagccgc cgcattgcat cagccatgat ggatactttc tcggcaggag   3420
caaggtgaga tgacaggaga tcctgccccg gcacttcgcc caatagcagc cagtcccttc    3480
ccgcttcagt gacaacgtcg agcacagctg cgcaaggaac gcccgtcgtg gccagccacg    3540
atagccgcgc tgcctcgtcc tgcagttcat tcagggcacc ggacaggtcg gtcttgacaa    3600
aaagaaccgg gcgcccctgc gctgacagcc ggaacacggc ggcatcagag cagccgattg    3660
tctgttgtgc ccagtcatag ccgaatagcc tctccaccca gcggccgga gaacctgcgt     3720 gcaatccatc ttgttcaatc atgcgaaacg atcctcatcc tgtctcttga tcagatcttg    3780 atccctgcg ccatcagatc cttggcggca agaaagccat ccagtttact ttgcaggggtt    3840 cccaacctta ccagagggcg ccccagctgg caattccggt tcgcttgctg tccataaaac    3900
cgcccagtct agctatcgcc atgtaagccc actgcaagct acctgctttc tctttgcgct    3960
tgcgttttcc cttgtccaga tagcccagta gctgacattc atccggggtc agcaccgttt    4020
ctgcggactg gctttctacg tgttccgctt cctttagcag cccttgcgcc ctgagtgctt    4080
gcggcagcgt gaagctagct tggcaatggc aacaacgttg cgcaaactat taactggcga    4140
actacttact ctagcttccc ggcaacaatt aatagactgg atggaggcgg ataaagttgc    4200
aggaccactt ctgcgctcgg cccttccggc tggctggttt attgctgata atctggagc     4260 cggtgagcgt gggtctcgcg gtatcattgc agcactgggg ccagatggta agccctcccg    4320
tatcgtagtt atctacacga cggggagtca ggcaactatg gatgaacgaa atagacagat    4380
cgctgagata ggtgcctcac tgattaagca ttggtaactg tcagaccaag tttactcata    4440
tatactttag attgatttaa aacttcattt ttaatttaaa aggatctagg tgaagatcct    4500
ttttgataat ctcatgcatg accaaaatcc cttaacgtga gttttcgttc cactgagcgt    4560 cagacccgt agaaaagatc aaaggatctt cttgagatcc ttttttttctg cgcgtaatct    4620 gctgcttgca acaaaaaaa ccaccgctac cagcggtggt ttgtttgccg gatcaagaga    4680
taccaactct ttttccgaag gtaactggct tcagcagagc gcagatacca aatactgtcc    4740
ttctagtgta gccgtagtta ggccaccact tcaagaactc tgtagcaccg cctacatacc    4800
tcgctctgct aatcctgtta ccagtggctg ctgccagtgg cgataagtcg tgtcttaccg    4860
ggtggactca agacgatagt taccggataa ggcgcagcgg tcgggctgaa cggggggttc    4920
gtgcacacag cccagcttgg agcgaacgac ctacaccgaa ctgagatacc taacagcgtg    4980
agctatgaga aagcgccacg cttcccgaag ggagaaaggc ggacaggtat ccggtaagcg    5040
gcagggtcgg aacaggagag cgcacagggg agcttccagg gggaaacgcc tggtatcttt    5100
atagtcctgt cgggtttcgc cacctctgac ttgagcgtcg attttttgtga tgctcgtcag    5160
```

```
ggggcggag cctatggaaa aacgccagca acgcggcctt tttacggttc ctggcctttt    5220
gctggccttt tgctcacatg ttctttcctg cgttatcccc tgattctgtg gataaccgta    5280
ttaccgcctt tgagtgagct gataccgctc gccgcagccg aacgaccgag cgcagcgagt    5340
cagtgagcga ggaagcggaa gagcgcctga tgcggtattt tctccttacg catctgtgcg    5400
gtatttcaca ccgcatagga attcgctaga gtcggaagca taaaagtgta aagcctgggg    5460
tgcctaatga gtgagctaac tcacatttaa ttgcgttgcg ctcactgccc gctttccagt    5520
cgggaaacct gtcgtgccag ctgcattaat gaatcggcca acgcgcgggg agaggcggtt    5580
tgcgtattgg gcgccagggt ggttttttctt ttcaccagtg acgggcaa cagctgattg    5640 cccttcaccg cctggccctg agagagttgc agcaagcggt ccacgctggt ttgccccagc    5700
aggcgaaaat cctgtttgat ggtggttgac ggcgggatat aacatgagct gtcttcggta    5760
tcgtcgtatc ccactaccga gatatccgca ccaacgcgca gcccggactc ggtaatggcg    5820
cgcattgcgc ccagcgccat ctgatcgttg caaccagca tcgcagtggg aacgatgccc    5880
tcattcagca tttgcatggt ttgttgaaaa ccggacatgg cactccagtc gccttcccgt    5940
tccgctatcg gctgaatttg attgcgagtg agatattttat gccagccagc cagacgcaga    6000
cgcgccgaga cagaacttaa tgggcccgct aacagcgcga tttgctggtg acccaatgcg    6060
accagatgct ccacgcccag tcgcgtaccg tcttcatggg agaaaataat actgttgatg    6120
ggtgtctggt cagagacatc aagaaataac gccggaacat tagtgcaggc agcttccaca    6180
gcaatggcat cctggtcatc cagcggatag ttaatgatca gcccactgac gcgttgcgcg    6240
agaagattgt gcaccgccgc tttacaggct tcgacgccgc ttcgttctac catcgacacc    6300
accacgctgg cacccagttg atcggcgcga gatttaatcg ccgcgacaat ttgcgacggc    6360
gcgtgcaggg ccagactgga ggtggcaacg ccaatcagca acgactgttt gcccgccagt    6420
tgttgtgcca cgcggttggg aatgtaattc agctccgcca tcgccgcttc cacttttcc    6480 cgcgttttcg cggaaacgtg gctggcctgg ttcaccacgc gggaaacggt ctgataagag    6540
acaccggcat actctgcgac atcgtataac gttactggtt tcacattcac caccctgaat    6600
tgactctctt ccgggcgcta tcatgccata ccgcgaaagg ttttgcgcca ttcgatggtg    6660
tcggcatgc                                                            6669
```

<210> SEQ ID NO 3
<211> LENGTH: 45
<212> TYPE: DNA
<213> ORGANISM: Artificial Sequence
<220> FEATURE:
<223> OTHER INFORMATION: synthetic

<400> SEQUENCE: 3

```
ggatctgcgc acgacactga acatacgaat ttaaggaata aacat             45
```

<210> SEQ ID NO 4
<211> LENGTH: 365
<212> TYPE: PRT
<213> ORGANISM: Pichia pastoris

<400> SEQUENCE: 4

```
Met Lys Ile Val Leu Val Leu Tyr Ser Ala Gly Lys His Ala Ala Asp
1               5                   10                  15

Glu Pro Lys Leu Tyr Gly Cys Ile Glu Asn Glu Leu Gly Ile Arg Gln
            20                  25                  30

Trp Leu Glu Lys Gly Gly His Glu Leu Val Thr Thr Ser Asp Lys Glu
```

```
                35                  40                  45
Gly Glu Asn Ser Glu Leu Glu Lys His Ile Pro Asp Ala Asp Val Ile
         50                  55                  60

Ile Ser Thr Pro Phe His Pro Ala Tyr Ile Thr Lys Glu Arg Ile Gln
 65                  70                  75                  80

Lys Ala Lys Lys Leu Lys Leu Val Val Ala Gly Val Gly Ser Asp
                 85                  90                  95

His Ile Asp Leu Asp Tyr Ile Glu Gln Asn Gly Leu Asp Ile Ser Val
                100                 105                 110

Leu Glu Val Thr Gly Ser Asn Val Val Ser Val Ala Glu His Val Val
                115                 120                 125

Met Thr Ile Leu Asn Leu Val Arg Asn Phe Val Pro Ala His Glu Gln
    130                 135                 140

Ile Val Asn His Gly Trp Asp Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Val Ala Phe Asn Pro Lys Glu Leu Leu
                180                 185                 190

Tyr Tyr Asp Tyr Gln Gly Leu Pro Lys Glu Ala Glu Lys Val Gly
            195                 200                 205

Ala Arg Arg Val Asp Thr Glu Glu Leu Val Ala Gln Ala Asp Val
    210                 215                 220

Val Thr Val Asn Ala Pro Leu His Ala Gly Thr Lys Gly Leu Val Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Asn Ala Gln Asp Val Ala Asp Ala Val Ala
                260                 265                 270

Ser Gly Gln Leu Arg Gly Tyr Gly Gly Asp Val Trp Phe Pro Gln Pro
            275                 280                 285

Ala Pro Lys Asp His Pro Trp Arg Asp Met Arg Asn Lys Tyr Gly Tyr
    290                 295                 300

Gly Asn Ala Met Thr Pro His Tyr Ser Gly Thr Thr Leu Asp Ala Gln
305                 310                 315                 320

Val Arg Tyr Ala Glu Gly Thr Lys Asn Ile Leu Asn Ser Phe Leu Thr
                325                 330                 335

Lys Lys Phe Asp Tyr Arg Pro Gln Asp Val Ile Leu Leu Asn Gly Lys
            340                 345                 350

Tyr Lys Thr Lys Ala Tyr Gly Asn Asp Lys Lys Val Ala
        355                 360                 365

<210> SEQ ID NO 5
<211> LENGTH: 378
<212> TYPE: PRT
<213> ORGANISM: Artificial Sequence
<220> FEATURE:
<223> OTHER INFORMATION: synthetic

<400> SEQUENCE: 5

Met Arg Asp Val Phe Glu Met Met Asp Arg Tyr Gly His Glu Gln Val
1               5                   10                  15

Ile Phe Cys Arg His Pro Gln Thr Gly Leu Lys Ala Ile Ile Ala Leu
                20                  25                  30

His Asn Thr Ala Gly Pro Ala Leu Gly Gly Cys Arg Met Ile Pro
            35                  40                  45
```

Tyr Ala Ser Thr Asp Glu Ala Leu Glu Asp Val Leu Arg Leu Ser Lys
 50                  55                  60

Gly Met Thr Tyr Lys Cys Ser Leu Ala Asp Val Asp Phe Gly Gly Gly
 65                  70                  75                  80

Lys Met Val Ile Ile Gly Asp Pro Lys Asp Lys Ser Pro Glu Leu
                 85                  90                  95

Phe Arg Val Ile Gly Arg Phe Val Gly Leu Asn Gly Arg Phe Tyr
                100                 105                 110

Thr Gly Thr Asp Met Gly Thr Asn Pro Glu Asp Phe Val His Ala Ala
                115                 120                 125

Arg Glu Ser Lys Ser Phe Ala Gly Leu Pro Thr Ser Tyr Gly Gly Ser
130                 135                 140

Gly Asp Thr Ser Ile Pro Thr Ala Leu Gly Val Phe His Gly Met Arg
145                 150                 155                 160

Ala Thr Ala Arg Phe Leu Trp Gly Thr Asp Gln Leu Lys Gly Arg Val
                165                 170                 175

Val Ala Ile Gln Gly Val Gly Lys Val Gly Glu Arg Leu Leu Gln Leu
                180                 185                 190

Leu Val Glu Val Gly Ala Tyr Cys Lys Ile Ala Asp Ile Asp Ser Val
                195                 200                 205

Arg Cys Glu Gln Leu Lys Glu Lys Tyr Gly Asp Lys Val Gln Leu Val
210                 215                 220

Asp Val Asn Arg Ile His Lys Glu Ser Cys Asp Ile Phe Ser Pro Cys
225                 230                 235                 240

Ala Lys Gly Gly Val Val Asn Asp Asp Thr Ile Asp Glu Phe Arg Cys
                245                 250                 255

Leu Ala Ile Val Gly Ser Ala Asn Asn Gln Leu Val Glu Asp Arg His
                260                 265                 270

Gly Ala Leu Leu Gln Lys Arg Ser Ile Trp Tyr Ala Pro Asp Tyr Leu
                275                 280                 285

Val Asn Ala Gly Gly Leu Ile Gln Val Ala Asp Glu Leu Glu Gly Phe
290                 295                 300

His Glu Glu Arg Val Leu Ala Lys Thr Glu Ala Ile Tyr Asp Met Val
305                 310                 315                 320

Leu Asp Ile Phe His Arg Ala Lys Asn Glu Asn Ile Thr Thr Cys Glu
                325                 330                 335

Ala Ala Asp Arg Ile Val Met Glu Arg Leu Lys Lys Leu Thr Asp Ile
                340                 345                 350

Arg Arg Ile Leu Leu Glu Asp Pro Arg Asn Ser Ala Glu Gly Tyr Leu
                355                 360                 365

Glu Pro Arg Arg Pro Arg Ile Asn Ser Pro
370                 375

<210> SEQ ID NO 6
<211> LENGTH: 24
<212> TYPE: DNA
<213> ORGANISM: Artificial Sequence
<220> FEATURE:
<223> OTHER INFORMATION: synthetic

<400> SEQUENCE: 6
aagcgagatc tgcgcacgac actg                                    24

<210> SEQ ID NO 7
<211> LENGTH: 26
<212> TYPE: DNA

```
<213> ORGANISM: Artificial Sequence
<220> FEATURE:
<223> OTHER INFORMATION: Synthetic

<400> SEQUENCE: 7
aattaattcg cggccgccgc ggctcg                                           26

<210> SEQ ID NO 8
<211> LENGTH: 1098
<212> TYPE: DNA
<213> ORGANISM: Pichia pastoris

<400> SEQUENCE: 8
atgaaaatcg ttctcgtttt gtactccgct ggtaagcacg ccgccgatga accaaagttg     60
tatggttgta tcgaaaatga attgggtatt agacaatggc ttgagaaggg cggccatgaa    120
ttggttacta catcagacaa agagggtgaa aactctgagt tagaaaagca cattcctgac    180
gctgatgtga ttatttccac tccattccat ccagcctaca tcacgaagga gagaatccaa    240
aaagccaaga agctgaagtt gttggtcgtt gctggtgtcg gttccgacca cattgacttg    300
gactacattg aacaaaatgg cctagatatt tcggtcctag aggttactgg ttccaacgtt    360
gtttcagtgg ctgagcatgt cgttatgact atattgaact tggtgagaaa ctttgttcca    420
gctcacgagc aaattgttaa ccacggctgg gacgttgctg ccatcgccaa ggacgcctac    480
gatatcgaag gtaagaccat cgcaacaatt ggtgctggaa gaattggtta cagagtctta    540
gagagacttg tggctttcaa ccctaaggaa ttgttgtact acgactacca aggtcttcca    600
aaagaggccg aggaaaaagt tggtgccaga gagtcgaca ctgtcgagga gctggttgct    660
caagccgatg ttgttaccgt caatgcccca ctgcacgcag gtactaaggg tttagttaac    720
aaggagcttc tgtccaagtt caagaagggt gcttggttgg ttaacacagc cagaggtgcc    780
atctgcaatg ctcaagatgt cgctgatgcc gttgcatctg gtcaattgag aggttacggt    840
ggtgacgtct ggttccctca gccagctcca aaggaccatc catggagaga tatgagaaac    900
aagtacggat acggaaacgc catgactcct cattactcag gtaccacttt ggacgcccag    960
gtcagatatg ccgaaggtac caagaacatc ttgaactcat tccttaccaa gaagtttgac   1020
tacagacctc aagatgtcat tctttttgaac ggtaagtaca agaccaaggc ttatggtaat   1080
gacaaaaagg tcgcataa                                                 1098

<210> SEQ ID NO 9
<211> LENGTH: 1137
<212> TYPE: DNA
<213> ORGANISM: Artificial Sequence
<220> FEATURE:
<223> OTHER INFORMATION: Synthetic

<400> SEQUENCE: 9
atgcgcgacg tgtttgaaat gatggaccgc tatggccacg agcaggtcat tttttgccgt     60
catccgcaaa ccggtctcaa agcgatcatc gccttgcata tacaaccgc ggggccggct    120
ttgggtggat gccgcatgat cccgtatgct tcgacggacg aagccttgga ggatgttttg    180
cggttgtcca aaggcatgac ctataaatgc agtctggcgg atgtggactt ggcggggga    240
aaaatggtta tcatcggcga tccgaaaaaa gataaatcgc cggagttgtt tcgcgtgatc    300
ggccgttttg tgggcgggtt aaacggccgt ttctataccg gaaccgacat gggaaccaat    360
ccggaagatt tgtccatgc cgccagggaa tcgaaatctt ttgccggatt gccgacatcg    420
tacggcggaa gcggggacac atccattccc accgcgctcg gggtgtttca cggaatgcgg    480
```

```
gccaccgccc ggtttttatg ggggacggat cagctgaaag ggcgtgtggt tgccatccaa      540
ggagtcggca aggtgggaga gcgcttgttg cagcttttgg tcgaagtggg ggcttactgc      600
aaaattgccg acatcgattc ggtgcgatgc gaacagctga aagaaaagta tggcgacaag      660
gtccaattgg tggatgtgaa ccggattcac aaggagagtt gcgatatttt ctcgccttgc      720 gccaaggcg gcgtggtcaa tgatgacacc attgacgagt tccgttgcct ggccattgtc       780
ggatccgcca caaccaact ggtggaagac cggcatgggg cactgcttca aaaacggagc        840
atttggtatg cacccgatta tctggtgaat gccggcgggc tgattcaagt ggctgatgaa      900
ctggaaggct tccatgaaga gagagtgctc gccaaaaccg aagcgattta tgacatggtc      960 ctggatatttt ttcaccgggc gaaaaatgag aatattacca cttgtgaggc agcggaccgg    1020
atcgtgatgg agcgtttgaa aaagttaacc gatattcgcc ggatcttgtt ggaggatccc     1080
cgcaacagcg cggaggggta cctcgagccg cggcggccgc gaattaattc gccttag       1137
```

GENETICALLY STABLE PLASMID EXPRESSING PDH AND FDH ENZYMES

This application is related to and claims priority to U.S. provisional application Ser. No. 61/167,676, filed Apr. 8, 2009, the disclosure of which is incorporated by reference herein.

The sequence listing is filed with the application in electronic format only (computer readable form) and is incorporated by reference herein. The sequence listing text file, "09-203-SEQ_LIST" [22,343 bytes in size], was created on Apr. 7, 2010.

BACKGROUND OF THE INVENTION

1. Field of the Invention

The invention relates to nucleic acid molecules, plasmids (e.g., bi-cistronic plasmids), host cells and methods used for the expression of formate dehydrogenase (FDH) and modified phenylalanine dehydrogenase (PDHmod).

2. Background of the Invention

Dipeptidyl peptidase IV is a membrane bound non-classical serine aminopeptidase which is located in a variety of tissues including, but not limited to, intestine, liver, lung, and kidney. This enzyme is also located on circulating T-lymphocytes wherein it is referred to as CD-26. Dipeptidyl peptidase IV is responsible for the metabolic cleavage of the endogenous peptides GLP-1(7-36) and glucagons in vivo and has demonstrated proteolytic activity against other peptides such as GHRH, NPY, GLP-2 and VIP in vitro.

GLP-1(7-36) is a 29 amino acid peptide derived from post-translational processing of proglucagon in the small intestine. This peptide has multiple actions in vivo. For example, GLP-1(7-36) stimulates insulin secretion and inhibits glucagon secretion. This peptide also promotes satiety and slows gastric emptying. Exogenous administration of GLP-1(7-36) via continuous infusion has been shown to be efficacious in diabetic patients. However, the exogenous peptide is degraded too rapidly for continual therapeutic use.

Inhibitors of dipeptidyl peptidase IV have been developed to potentiate endogenous levels of GLP-1(7-36). U.S. Pat. No. 6,395,767 discloses cyclopropyl-fused pyrrolidine-based inhibitors of dipeptidyl peptidase IV. Methods for chemically synthesizing these inhibitors are disclosed in U.S. Pat. No. 6,395,767 as well as in the literature. For example, see Sagnard et al. *Tetr. Lett.* 1995 36:3148-3152; Tverezovsky et al. *Tetrahedron* 1997 53:14773-14792; and Hanessian et al. *Bioorg. Med. Chem. Lett.* 1998 8:2123-2128. An example of an inhibitor disclosed in U.S. Pat. No. 6,395,767 is the free base, (1S,3S,5S)-2-[(2S)-2-amino-2-(3-hydroxy-tricyclo [3.3.1.1$^{3,7}$]dec-1-yl)-1-oxoethyl]-2-azabicyclo-[3.1.0]hexane-3-carbonitrile.

Methods for preparing intermediates used in the production of this dipeptidyl peptidase IV inhibitor are disclosed in EP 0 808 824 A2. Also see, Imashiro and Kuroda *Tetrahedron Letters* 2001 42:1313-1315, Reetz et al. *Chem. Int. Ed. Engl.* 1979 18:72, Reetz and Heimbach *Chem. Ber.* 1983 116:3702-3707, Reetz et al. *Chem. Ber.* 1983 116:3708-3724.

Recombinant expression of the enzymes formate dehydrogenase (FDH) (e.g., from *Pichia pastoris* (ATCC 20864)) and phenylalanine dehydrogenase (PDH) (e.g., from *Thermoactinomyces intermedius* (ATCC 33205)) can be used in the biotransformation of 3-hydroxy-α-oxotricyclo-[3.3.1.1$^{3,7}$] decane-1-acetic acid to (αS)-α-amino-3-hydroxytricyclo [3.3.1.1$^{3,7}$] decane-1-acetic acid which is then chemically converted to (αS)-α-[[(1,1 dimethylethoxy)carbonyl] amino]-3-hydroxytricyclo[3.3.1.1$^{3,7}$] decane-1-acetic acid, a starting material in the synthesis of the DPPIV inhibitor, saxagliptin. Previous attempts to express FDH and PDH using a single plasmid containing two identical tandem promoters (one promoter for each enzyme) to drive expression have had limited success. In particular, prior attempts appear to have resulted in bacterial cultures harboring two different populations of bacterial cell: one containing an intact plasmid, and another wherein the portion of the plasmid containing the FDH gene appears to have been processed (truncated). The processing of the plasmid appears to have increased with each cell generation.

Thus, while biotransformation methods have been identified as a method for generating complex chemical precursors, the biosynthetic processes discussed above suffer decreased product yield because of genetic instability. Thus, there is a need for alternative recombinant sequences and methods for generating synthetic precursor molecules in the eventual production of chemical compounds, such as saxagliptin.

SUMMARY OF THE INVENTION

In an aspect, the disclosure relates to an isolated nucleic acid molecule comprising:
  (a) an isolated nucleic acid sequence comprising a nucleotide sequence that is 95% identical to SEQ ID NO: 1; or
  (b) a sequence encoding the polypeptide of SEQ ID NO: 4 and the polypeptide of SEQ ID NO: 5.

In an aspect, the disclosure relates to an isolated nucleic acid molecule comprising the nucleotide sequence of SEQ ID NO: 1.

In an aspect, the disclosure relates to an isolated nucleic acid molecule comprising a sequence that hybridizes to the complement of the nucleotide sequence of SEQ ID NO: 1 under stringent hybridization conditions.

In an aspect, the disclosure relates to an isolated nucleic acid molecule comprising the nucleotide sequence of SEQ ID NO: 2.

In an aspect, the disclosure relates to a plasmid comprising a nucleic acid molecule comprising SEQ ID NO: 1.

In an aspect, the disclosure relates to an isolated host cell comprising a nucleic acid molecule comprising SEQ ID NO: 1.

In an aspect, the disclosure relates to an isolated host cell comprising a nucleic acid molecule comprising SEQ ID NO: 2.

In an aspect, the disclosure relates to a method for producing (αS)-α-[[(1,1-dimethylethyoxy)carboxyl]-amino]-3-hydroxytricyclo[3.3.1.1$^{3,7}$]decane-1-acetic acid (Formula I):

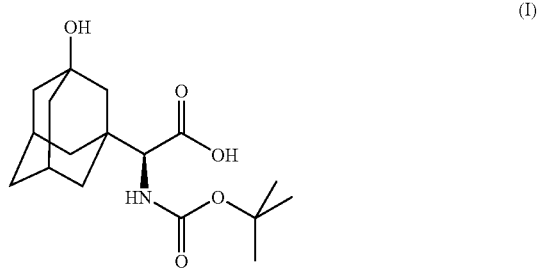

(I)

wherein the method comprises:
  (a) culturing the host cell of claim 8 under suitable conditions to express the polypeptides encoded by the nucleic acid molecule of SEQ ID NO: 1;

(b) partially purifying an enzyme concentrate comprising the polypeptides; and (c) contacting the culture isolate with an amount of 3-hydroxy-α-oxotricyclo-[3.3.1.1$^{3,7}$]decane-1-acetic acid (Formula II):

(II)

under conditions that allow for production of (αS)-α-amino-3-hydroxytricyclo[3.3.1.1$^{3,7}$]decane-1-acetic acid (Formula III):

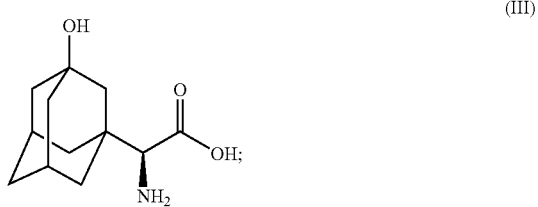

(III)

and (d) contacting the (αS)-α-amino-3-hydroxytricyclo [3.3.1.1$^{3,7}$]decane-1-acetic acid with an amount of di-tent-butyl dicarbonate under conditions that allow for production of (αS)-α-[[(1,1-dimethylethyoxy)carboxyl]-amino]-3-hydroxytricyclo[3.3.1.1$^{3,7}$]decane-1-acetic acid (Formula I).

In an aspect, the disclosure relates to a process of preparing a partially purified enzyme concentrate of phenylalanine dehydrogenase (PDH) and formate dehydrogenase (FDH), wherein the process comprises preparing a fermentation broth containing a cell containing a nucleic acid molecule or plasmid as described herein.

The above aspects as well as other aspect and embodiments will become apparent to those of skill in the art in view of the following detailed description.

BRIEF DESCRIPTION OF THE DRAWINGS

FIG. 2 shows the nucleic acid sequences of the FDH/PDHmod bi-cistronic plasmid (SEQ ID NO: 2). The region encoding FDH (SEQ ID NO: 8), the ribosome binding site (SEQ ID NO: 3) and PDHmod (SEQ ID NO: 9), is underlined in bold (SEQ ID NO: 1).

DETAILED DESCRIPTION OF THE INVENTION

Figure 1:
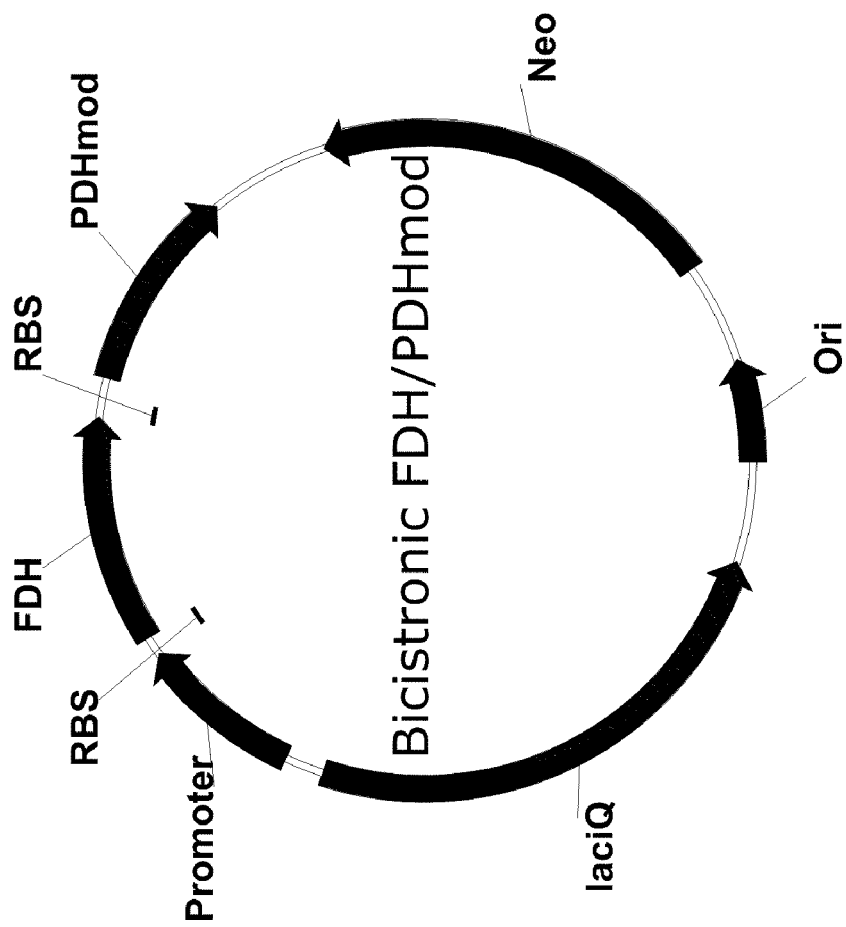
FIG. 1 shows a schematic of the Bi-cistronic FDH/PDH-mod Plasmid.

In a general sense, the disclosure relates to nucleic acid molecules, plasmids, vectors, host cells, and methods that provide for the biotransformation of chemical molecules to useful synthetic precursor molecules and/or intermediates in the production of desirable chemical compounds (e.g., drug products such as the DPPIV inhibitor, saxagliptin). The nucleic acid molecule can be incorporated into a vector, such as an expression vector or plasmid, and provides for a recombinant construct that is stable genetically in a host cell, (e.g., a bacterial cell). The cells and plasmids find use in methods that comprise formate dehydrogenase and phenylalanine dehydrogenase activity.

Definitions

Before describing the various aspects and embodiments of the disclosure in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the invention as claimed or to imply that certain features are critical, essential, or even important to the structure or function of the claimed invention. Rather, any use of these terms is merely intended to highlight alternative or additional features that can or can not be utilized in a particular embodiment.

In some instances the disclosure may use the terms "substantially" or "about" to represent the inherent degree of uncertainty that can be attributed to any quantitative comparison, value, measurement, or other representation. The terms may also represent the degree by which a quantitative representation can vary from a stated reference without resulting in a change in the basic function of the subject matter at issue.

As used herein, the terms "polynucleotide", "nucleotide", "oligonucleotide", and "nucleic acid molecule" can be used interchangeably to refer to nucleic acid molecule comprising DNA, RNA, derivatives thereof, or combinations thereof.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man. When used in connection with nucleotides, the terms "naturally occurring" or "native" refer to the bases adenine (A), cytosine (C), guanine (G), thymine (T), and uracil (U). When used in connection with amino acids, the terms "naturally occurring" and "native" refer to the 20 amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y).

The term "phenylalanine dehydrogenase" or "PDH" means a protein having phenylalanine dehydrogenase activity, as well as enzymatically active fragments and variants thereof. A non-limiting example of PDH is "PDHmod" that comprises SEQ ID NO: 5 that has phenylalanine dehydrogenase activity, as well as enzymatically active fragments and variants of SEQ ID NO: 5.

The term "formate dehydrogenase" or "FDH" means a protein having formate dehydrogenase activity, as well as enzymatically active fragments and variants thereof. A non-limiting example of FDH comprises SEQ ID NO: 4 that has formate dehydrogenase activity, as well as enzymatically active fragments and variants of SEQ ID NO: 4.

Nucleic Acids, Plasmids, and Host Cells

The recombinant DNA methods used herein are generally those set forth in Sambrook et al., Molecular Cloning: A Laboratory Manual (Cold Spring Harbor Laboratory Press, 1989) and/or *Current Protocols in Molecular Biology* (Ausubel et al., eds., Green Publishers Inc. and Wiley and Sons 1994).

In an aspect, the disclosure provides an isolated nucleic acid molecule comprising SEQ ID NO: 1, or a sequence encoding a functional formate dehydrogenase and a functional phenylalanine dehydrogenase. In embodiments the formate dehydrogenase (FDH) can comprise any FDH sequence, or functional fragment thereof, from any particular species. In embodiments the phenylalanine dehydrogenase (PDH) can be any PDH sequence, or functional fragment thereof, from any particular species. In an embodiment the FDH sequence comprises SEQ ID NO: 4, or a functional fragment or variant thereof. In an embodiment the PDH sequence comprises SEQ ID NO: 5, or a functional fragment or variant thereof. In an embodiment, the nucleic acid molecule comprises the nucleotide sequence of SEQ ID NO: 1.

In embodiments, the nucleic acid molecule comprises a single promoter region that directs expression of the regions encoding FDH and PDH, wherein the promoter region is as described herein below.

In embodiments the nucleic acid molecule comprises a region between the portion of the molecule encoding FDH and PDH. In embodiments, the region comprises a length of about 10 to about 100 nucleotides (e.g., about 10, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 nucleotide bases). In embodiments, the region comprises a ribosome binding site as described herein below.

The term "isolated nucleic acid molecule" refers to a nucleic acid molecule that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Accordingly, in various embodiments, the isolated nucleic acid molecule is substantially free from any other contaminating nucleic acid molecule(s) or other contaminants that are found in its natural environment that would interfere with its use in polypeptide production or its therapeutic, diagnostic, prophylactic or research use. In certain embodiments, the isolated nucleic acid molecule is contained within a cell.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

In an aspect, the disclosure provides an isolated nucleic acid sequence comprising a nucleotide sequence that is 95% identical to SEQ ID NO: 1.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

In an embodiment, the isolated nucleic acid sequence comprises a nucleotide sequence that hybridizes to the complement of the nucleotide sequence of SEQ ID NO: 1 at 42° C. in a hybridization buffer comprising 50% formamide, 5×SSC (0.75 M NaCl, 0.075 M sodium citrate), 50 mM sodium phosphate (pH 6.8), 0.1% sodium pyrophosphate, 0.1% SDS, and 10% dextran sulfate, and then at 42° C. in a hybridization wash buffer comprising 0.2×SSC and 0.1% SDS.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melt ing temperature of a perfectly matched DNA duplex can be estimated by the following equation:

$$T_m(°C.)=81.5+16.6(\log [Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid.

For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm=2° C. \text{ per } A\text{-}T \text{ base pair}+4° C. \text{ per } G\text{-}C \text{ base pair}$$

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6×SSC, 0.1% SDS.

In an aspect, the disclosure provides a plasmid comprising the nucleic acid molecule of SEQ ID NO: 1.

In another aspect, the disclosure provides a plasmid comprising a sequence encoding the polypeptide of SEQ ID NO: 4 and the polypeptide of SEQ ID NO: 5.

The term "plasmid" is used to refer to any molecule (e.g., nucleic acid, vector, or virus) used to transfer coding information to a host cell.

The term "expression plasmid" refers to a plasmid that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present. In general, plasmid molecules (e.g., expression vectors, host vectors, etc.) are known in the art and are commercially available.

In embodiments, the plasmid is designed to comprise the nucleic acid as described herein wherein the expression of FDH and PDH is under the control of a single promoter.

In various embodiments, expression plasmids used in any of the host cells can contain sequences for plasmid maintenance and for cloning and expression of exogenous nucleotide sequences. Such sequences, collectively referred to as "flanking sequences" in certain embodiments, will typically include one or more of the following nucleotides: a promoter, an origin of replication, a transcriptional termination sequence, a leader sequence for secretion in the case of expression of secretable protein, a ribosome binding site, a polylinker region for inserting the nucleic acid encoding the polypeptide to be expressed, and a selectable marker element.

Optionally, the plasmid may contain a "tag" sequence, i.e., an oligonucleotide molecule located at the 5' or 3' end of the FDH or PDHmod polypeptide coding sequence; the oligonucleotide molecule encodes polyHis (such as hexaHis), or other "tag" such as FLAG, HA (hemaglutinin Influenza virus) or myc for which commercially available antibodies exist. This tag can be fused to the polypeptide upon expression of the polypeptide, and can serve as a means for affinity purification of the PHDmod or FDH polypeptides from the host cell. Affinity purification can be accomplished, for example, by column chromatography using antibodies against the tag as an affinity matrix. Optionally, the tag can subsequently be removed from the purified PHDmod or FDH polypeptides by various means such as using certain peptidases for cleavage.

A transcription termination sequence is typically located 3' of the end of a polypeptide coding regions and serves to terminate transcription. Usually, a transcription termination sequence in prokaryotic cells is a G-C rich fragment followed by a poly-T sequence. While the sequence is easily cloned from a library or even purchased commercially as part of a plasmid, it can also be readily synthesized using methods for nucleic acid synthesis such as those described above.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

In an aspect, the disclosure provides an isolated host cell comprising a bi-cistronic plasmid, wherein the plasmid codes for FDH and PDHmod. A host cell can be any suitable host cell and selected by one of skill based on the desired application (e.g., for amplification and/or polypeptide expression).

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

In certain embodiments, selection pressure is imposed by culturing the transformed cells under conditions in which the concentration of selection agent in the medium is successively changed, thereby leading to amplification of both the selection gene and the DNA that encodes PDHmod and FDH polypeptides. As a result, increased quantities of PDHmod and FDH polypeptides are synthesized from the amplified DNA.

Transformation or transfection of an expression plasmid for PDHmod and FHD polypeptides into a selected host cell may be accomplished by well known methods including methods such as calcium chloride, electroporation, microinjection, lipofection or the DEAE-dextran method. The method selected will in part be a function of the type of host cell to be used. These methods and other suitable methods are well known in the art, and are set forth, for example, in Sambrook et al., supra.

A selectable marker gene element encodes a protein necessary for the survival and growth of a host cell grown in a selective culture medium. Typical selection marker genes encode proteins that (a) confer resistance to antibiotics or other toxins, for example, ampicillin, tetracycline, or kanamycin for prokaryotic host cells, (b) complement auxotrophic deficiencies of the cell; or (c) supply critical nutrients not available from complex media. Examples of selectable markers are the kanamycin resistance gene, the ampicillin resistance gene, and the tetracycline resistance gene. A neomycin resistance gene may also be used for selection in prokaryotic and eukaryotic host cells.

Nucleic acid molecules encoding PDH or PHDmod and FDH polypeptides are inserted into an appropriate expression plasmid using standard ligation techniques. The plasmid may be selected to be functional in the particular host cell employed (i.e., the plasmid is compatible with the host cell machinery such that amplification of the gene and/or expression of the gene can occur).

In a further embodiment, the nucleic acid molecules can be amplified and/or expressed in prokaryotic host cells. Host cells can be prokaryotic host cells (such as *E. coli*). The host cell, when cultured under appropriate conditions, synthesizes PDHmod and FDH polypeptides which can subsequently be collected directly from the host cell producing it. Selection of an appropriate host cell will depend upon various factors, such as desired expression levels, polypeptide modifications that are desirable or necessary for activity, such as glycosylation or phosphorylation, and ease of folding into a biologically active molecule.

Bacterial cells are useful as host cells suitable for the nucleic acid molecule and/or plasmid as described herein. In various embodiments, the host cell can comprise any various strain of *E. coli* (e.g., JM110, HB101, DH5, DH10, and MC1061). In embodiments, cells comprising the nucleic acid or plasmid (i.e., transformed or transfected) may be cultured using standard media well known in the art. The media will usually contain all nutrients necessary for the growth and survival of the cells. Suitable media for culturing *E. coli* cells are for example, Luria Broth (LB) and/or Terrific Broth (TB). In several embodiments, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

In some embodiments, a ribosome binding site (RBS) can initiate translation of mRNA in prokaryotes and is characterized by a Shine-Dalgarno sequence. In embodiments, the RBS can be located 3' to the promoter and 5' to the coding sequence of the PDH and FDH polypeptides to be expressed. The expression of native proteins in an unfused state can be inhibited by formation of local secondary structures with regions containing the Shine-Dalgarno sequence and/or mRNA start codons such that ribosomes cannot initiate translation. In embodiments, the plasmid can be used to overcome this translational inhibition of mRNAs containing eukaryotic sequences (Yero et al., *Biotechnol. Appl. Biochem.*, 44:27-34, (2006); Schoner et al., *Proc. Natl. Acad. Sci. U.S.A,* 83:8506-8510 (1986)).

The expression and cloning plasmids can, in various embodiments, contain a promoter that is recognized by the host organism and operably linked to the molecule encoding the FDH polypeptide. Promoters are untranslated sequences located upstream (i.e., 5') of the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. A large number of promoters, recognized by a variety of potential host cells, are well known. These promoters are operably linked to the DNA encoding FDH polypeptide by removing the promoter from the source DNA by restriction enzyme digestion and inserting the desired promoter sequence into the plasmid. The native FDH promoter sequence may be used to direct amplification and/or expression of FDH and PDHmod DNA. A heterologous promoter may be used in certain embodiments if it permits greater transcription and higher yields of the expressed protein as compared to the native promoter, and if it is compatible with the host cell system that has been selected for use.

Promoters suitable for use with prokaryotic hosts include the beta-lactamase (Villa-Kamaroff et al., *Proc. Natl. Acad. Sci. U.S.A.,* 75:3727-31 (1978)) and lactose promoter systems; alkaline phosphatase, the tryptophan (trp) promoter system; and hybrid promoters such as the tac promoter (DeBoer et al., *Proc. Natl. Acad. Sci. U.S.A.,* 80:21-25 (1983)). Other known bacterial promoters are also suitable. Their sequences have been published, and are well known in the art. These sequences may be ligated to the desired DNA sequence, using linkers or adapters as needed to supply any required restriction sites.

Several plasmids which are compatible with bacterial hosts may be used in various embodiments. Such plasmids include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.). The recombinant molecules can be introduced into host cells via transformation, transfection, infection, electroporation, or other known techniques.

Polypeptide Production

The FDH (SEQ ID NO: 4) and PDHmod (SEQ ID NO: 5) enzymes that are used in various embodiments, are oxireductase enzymes that catalyze NAD-dependent oxidation reactions.

In an aspect, the disclosure provides a process for producing the polypeptides of SEQ ID NO: 4 and SEQ ID NO: 5, comprising culturing a host cell comprising the plasmid described herein under suitable conditions to express the polypeptides.

In an embodiment the disclosure provides a process of preparing a partially purified enzyme concentrate of phenylalanine dehydrogenase (PDH) and formate dehydrogenase (FDH), wherein the process comprises preparing a fermentation broth containing a cell containing a nucleic acid molecule or plasmid as described herein; microfluidizing the fermentation broth while maintaining the temperature of said fermentation broth between about 4° C. and 30° C. to form a microfluidized broth containing the PDH and FDH; clarifying the microfluidized broth by treating the broth with a flocculating agent to coagulate cell debris and remove DNA and unwanted proteins, thereby forming a clarified broth; filtering the clarified broth to give a filtrate; and optionally concentrating the filtrate to give said partially purified enzyme concentrate, wherein the concentrate comprises a PDH activity of about 400 IU/ml to about 1000 IU/ml and a FDH activity of about 20 IU/ml to about 200 IU/ml. In embodiments, the enzyme concentrate is capable of reductively aminating a keto-containing compound into a chiral amine-containing compound, wherein said chiral amine-containing compound, without isolation from the enzyme concentrate, is capable of being BOC-protected. In embodiments, the clarifying can optionally comprise contacting the microfluidized broth with diatomaceous earth and the filtering comprises filtering the diatomaceous earth with a filter press.

In embodiments the cell comprises a nucleic acid molecule comprising a sequence that is 95% identical to SEQ ID NO:1. In embodiments the cell comprises a nucleic acid molecule comprising SEQ ID NO:1. In embodiments the cell comprises a nucleic acid molecule having a sequence that encoding the polypeptide of SEQ ID NO:4 and the polypeptide of SEQ ID NO:5. In embodiments the cell comprises a nucleic acid molecule comprising a sequence that hybridizes to the complement of the nucleotide sequence of SEQ ID NO: 1 at 42° C. in a hybridization buffer comprising 50% formamide, 5×SSC (0.75 M NaCl, 0.075 M sodium citrate), 50 mM sodium phosphate (pH 6.8), 0.1% sodium pyrophosphate, 0.1% SDS, and 10% dextran sulfate, and then at 42° C. in a hybridization wash buffer comprising 0.2×SSC and 0.1% SDS. In embodiments the cell comprises a nucleic acid molecule comprising SEQ ID NO:2.

The process can comprise any effective range of pressures for microfluidizing the fermentation broth such as, for example, a pressure ranging anywhere from about 12,000 to about 20,000 psi. The method can comprise any temperature that is effective to maintain the overall health of the cell and/or the activity of the PDH and FDH enzymes. While temperature ranges can be determined by one of skill in the art, non-limiting examples of temperatures include between about 4° C. and 25° C. or between about 8° C. and 25° C. The cell used in the method can be any cell that can stably harbor the nucleic acid molecule and/or plasmid described herein, and expresses PDH and FDH under appropriate conditions. In embodiments, the cell is *Escherichia coli* JM110.

The process can include any effective filtering method that is known in the art such as, for example, ultrafiltration using an ultrafiltration membrane or cassette. Similarly, the process can include any clarifying process steps that can include a flocculating agent, and or a decolorizing agent that is effective to remove DNA and unwanted protein (e.g., by coagulating cell debris).

The term "isolated polypeptide" refers to a polypeptide that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The amount of PDHmod and FDH polypeptides produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

Purification of PDHmod and FDH polypeptides from solution can be accomplished using a variety of techniques. If the polypeptide has been synthesized such that it contains a tag such as Hexahistidine or other small peptide such as FLAG (Eastman Kodak Co., New Haven, Conn.) or myc (Invitrogen) at either its carboxyl or amino terminus, it may essentially be purified in a one-step process by passing the solution through an affinity column where the column matrix has a high affinity for the tag or for the polypeptide directly (i.e., a monoclonal antibody specifically recognizing PDHmod or FDH polypeptide). For example, polyhistidine binds with great affinity and specificity to nickel and thus an affinity column of nickel (such as the QIAGEN® nickel columns) can be used for purification of FDH or PDHmod polypeptide/polyHis. See e.g., *Current Protocols in Molecular Biology* §10.11.8 (Ausubel et al., eds., John Wiley & Sons 1993).

Where FDH or PDH polypeptide is prepared without a tag attached, and no antibodies are available, other well-known procedures for purification can be used. Such procedures include, without limitation, ion exchange chromatography, molecular sieve chromatography, fractionation by ammonium sulfate precipitation, HPLC, native gel electrophoresis in combination with gel elution, and preparative isoelectric focusing ("Isoprime" machine/technique, Hoefer Scientific). In some cases, two or more of these techniques may be combined to achieve increased purity.

In some cases, FDH or PDHmod polypeptides may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-mercaptoethanol(bME)/dithio-b(ME). In many instances, a cosolvent may be used or may be needed to increase the efficiency of the refolding and the more common reagents used for this purpose include glycerol, polyethylene glycol of various molecular weights, arginine and the like.

If inclusion bodies are not formed to a significant degree upon expression of FDH or PDHmod polypeptides, the polypeptides will be found primarily in the supernatant after centrifugation of the cell homogenate and may be further isolated from the supernatant using methods such as those set forth below.

In situations where it is preferable to partially or completely purify FDH or PDHmod polypeptide such that it is partially or substantially free of contaminants, standard methods known to the one skilled in the art may be used. Such methods include, without limitation, separation by electrophoresis followed by electroelution, various types of chromatography (affinity, immunoaffinity, molecular sieve, and/or ion exchange), and fractionation by ammonium sulfate precipitation and/or high pressure liquid chromatography. In some cases, it may be preferable to use more than one of these methods for complete purification.

The term "similarity" is a related concept to identity, but in contrast to "identity," "similarity" refers to a measure of relatedness that includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Differences in the nucleic acid sequence may result in conservative and/or non-conservative modifications of the amino acid sequence relative to the amino acid sequence of either SEQ ID NO: 4 or SEQ ID NO: 5.

Conservative modifications to the amino acid sequence of either SEQ ID NO: 4 or SEQ ID NO: 5 (and the corresponding modifications to the encoding nucleotides) will produce a polypeptide having functional and chemical characteristics similar to those of FDH or PDHmod polypeptides. In contrast, substantial modifications in the functional and/or chemical characteristics of FDH or PDHmod polypeptides may be accomplished by selecting substitutions in the amino acid sequence of either SEQ ID NO: 4 or SEQ ID NO: 5 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, in certain embodiments the substitutions of amino acids are those whose hydropathic indices are within ±2, within ±1, and within ±0.5.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, in certain embodiments the substitutions of amino acids are those whose hydropathic values are within ±2, within ±1, and within ±0.5.

One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the FDH or PDHmod polypeptides described herein. Exemplary amino acid substitutions are set forth in Table I.

TABLE I

AMINO ACID SUBSTITUTIONS

| Original Residues | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4 Diamino-butyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

A skilled artisan will be able to determine suitable variants of the polypeptide as set forth in either SEQ ID NO: 4 or SEQ ID NO: 5 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a FDH or PDHmod polypeptides to such similar polypeptides. With such a comparison, one can identify residues and portions of the molecules that are conserved among similar polypeptides. It will be appreciated that changes in areas of the FDH or PDHmod molecule that are not conserved relative to such similar polypeptides would be less likely to adversely affect the biological activity and/or structure of a FDH or PDHmod polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a FDH or PDHmod polypeptide that correspond to amino acid residues that are important for activity or structure in similar polypeptides. One skilled in the art may opt for chemically similar amino acid substitutions for such predicted important amino acid residues of FDH or PDHmod polypeptides.

One skilled in the art can also analyze the three-dimensional structure and amino acid sequence in relation to that structure in similar polypeptides. In view of such information, one skilled in the art may predict the alignment of amino acid residues of FDH or PDHmod polypeptide with respect to its three dimensional structure. One skilled in the art may choose not to make radical changes to amino acid residues predicted to be on the surface of the protein, since such residues may be involved in important interactions with other molecules.

Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol. Relat. Areas Mol. Biol.* 47:45-48; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins that have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science*, 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heijne, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Certain methods to determine identity and/or similarity are designed to give the largest match between the sequences tested. Methods to determine identity and similarity are described in publicly available computer programs. Certain computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences and this small aligned region may have very high sequence identity even though there is no significant relationship between the two full-length sequences. Accordingly, in one embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci. USA* 89:10915-19 (BLOSUM 62 comparison matrix)).

Parameters that may be used for polypeptide sequence comparison include the following:
Algorithm: Needleman and Wunsch, 1970, *J. Mol. Biol.* 48:443-53;
Comparison matrix: BLOSUM 62 (Henikoff et al., supra);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Parameters that may be used for nucleic acid molecule sequence comparison include the following:
Algorithm: Needleman and Wunsch, supra;
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are may be used) or between one sequence and a large database of sequences (in which case FASTA or BLASTA are may be used).

In an aspect, the disclosure relates to a method for producing a precursor to saxagliptin, comprising, culturing a host cell containing the nucleic acid molecule and/or plasmid (e.g., a bi-cistronic plasmid) as described herein under suitable conditions to express the FDH and PDHmod; isolating the polypeptides from the culture; and using the isolated polypeptides for a reductive amination reaction.

The plasmid disclosed herein, remains genetically stable after 9 consecutive sub-cultivations (~60-70 generations), which is more extensive than from a frozen cell bank vial to the end of production fermentation (~15-20 generations).

In an aspect, the disclosure provides a method for producing (αS)-α-[[(1,1-dimethylethyoxy)carboxyl]-amino]-3-hydroxytricyclo[3.3.1.1$^{3,7}$]decane-1-acetic acid comprising: culturing the host cell described herein under suitable conditions to express the polypeptides; isolating a culture isolate comprising the polypeptides; and contacting the culture isolate with an amount of 3-hydroxy-α-oxotricyclo-[3.3.1.1$^{3,7}$]decane-1-acetic acid and an amount of di-tent-butyl dicarbonate under conditions that allow for production of (αS)-α-[[(1,1-dimethylethyoxy)carboxyl]-amino]-3-hydroxytricyclo[3.3.1.1$^{3,7}$]decane-1-acetic.

In an embodiment, the method comprises producing (αS)-α-[[(1,1-dimethylethyoxy)carboxyl]-amino]-3-hydroxytricyclo[3.3.1.1$^{3,7}$]decane-1-acetic acid (Formula I):

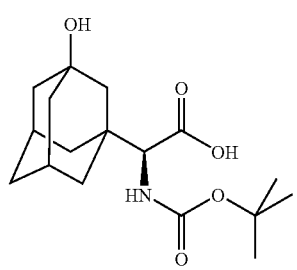

(I)

by culturing a host cell described herein under suitable conditions to express the FDH and PDH polypeptides; isolating a culture isolate comprising the polypeptides; and contacting the culture isolate with an amount of 3-hydroxy-α-oxotricyclo-[3.3.1.1$^{3,7}$]decane-1-acetic acid (Formula II):

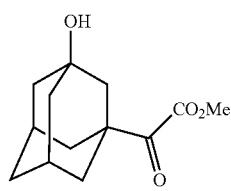

(II)

under conditions that allow for production of (αS)-α-amino-3-hydroxytricyclo[3.3.1.1$^{3,7}$]decane-1-acetic acid (Formula III):

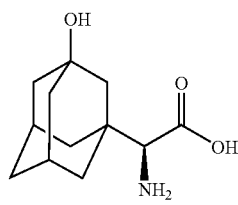

(III)

and contacting the (αS)-α-amino-3-hydroxytricyclo[3.3.1.1$^{3,7}$]decane-1-acetic acid with an amount of di-tent-butyl dicarbonate under conditions that allow for production of (αS)-α-[[(1,1-dimethylethyoxy)carboxyl]-amino]-3-hydroxytricyclo[3.3.1.1$^{3,7}$]decane-1-acetic acid. Various reaction conditions that can be used in the methods described herein have been detailed elsewhere and are known generally in the art. See U.S. Pat. No. 7,420,079. The Examples that follow are illustrative of specific embodiments of the disclosure, and various uses thereof. They are set forth for explanatory purposes only, and are not to be taken as limiting the invention, which is detailed in the appended claims. All patent and non-patent literature references that are referred to herein are incorporated by reference in their entirety.

EXAMPLE 1

Construction of the Bi-Cistronic FDH/PDHmod Plasmid

The bi-cistronic FDH/PDHmod plasmid was constructed by the insertion of a PCR amplified fragment containing the PDHmod gene with a 5' ribosome binding sequence (SEQ ID NO: 3) into the pBMS2000-PPFDH-PDHmod plasmid from which the PDHmod gene and its corresponding promoter had been removed. The pBMS2000-PPFDH-PDHmod plasmid was originally disclosed in U.S. Pat. No. 7,420,079, with its pre-curser, the pBMS2000 plasmid, originally disclosed in U.S. Pat. No. 6,068,991. Both of these patents are herein incorporated by reference.

The pBMS2000-PPFDH-PDHmod plasmid was digested with BamHI and NoI restriction enzymes to remove the PDHmod gene and its promoter. The digested DNA was separated on an agarose gel and the 5.5 Kb fragment was isolated using the QIAGEN® gel extraction procedure.

A forward primer, pdhmod1f (5'-AAGCGAGATCTGCG-CACGACACTG-3'; SEQ ID NO: 6) was designed to amplify the PDHmod sequence with the 5' ribosome binding site and a BglII site for ligation with the BamHI site of the vector. The reverse primer, pdhmod3r (5'-AATTAATTCGCGGCCGC-CGCGGCTCG-3'; SEQ ID NO: 7) was designed 3' to a NoI site in the template, plasmid pBMS2000-PDHmod, so that a BglII/NotI double digest of the PCR product results in a fragment that could be inserted immediately 3' to the FDH sequence in the digested vector. A PCR reaction was performed using 10 pmoles each of forward and reverse primer, the vector template, pBMS2000-PDHmod, and the HF Polymerase enzyme (CLONTECH®), according to the manufacturer's protocol. The reaction was performed in a 9700 thermocycler (APPLIED BIOSYSTEMS®). The PCR products were purified using a QIAGEN® PCR clean-up column and eluted in 50 µL of TE. The PCR product was digested with BglII and NoI restriction enzymes, separated on an agarose gel and the ~1.2 kb band excised and purified using a QIAGEN® gel extraction kit.

The BglII/NotI digested PCR fragment, containing the PDHmod gene was ligated to the BamHI/NotI digested plasmid containing the FDH gene sequence and promoter, using T4 DNA ligase. One µL of the ligation was transformed to MachI competent cells (INVITROGEN®) and plated to Luria Broth (LB) plates with 30 µg/mL kanamycin. Plasmid minipreps were performed and plasmids of the expected size were confirmed by agarose gel analysis.

Plasmid DNA was sequenced using dye-deoxy terminator chemistry (APPLIED BIOSYSTEMS®). Primers were designed to sequence the entire inserted PCR fragment (BglII/NotI fragment) and the junction with the digested vector sequence. The intergenic sequence between the terminator of the FDH gene and the start of the PDHmod sequence was as expected. The bi-cistronic FDH/PDHmod plasmid was transformed to the E. coli expression host JM110.

EXAMPLE 2

Confirmation of Stability of Bi-Cistronic FDH/PDHmod Plasmid

Figure 3:
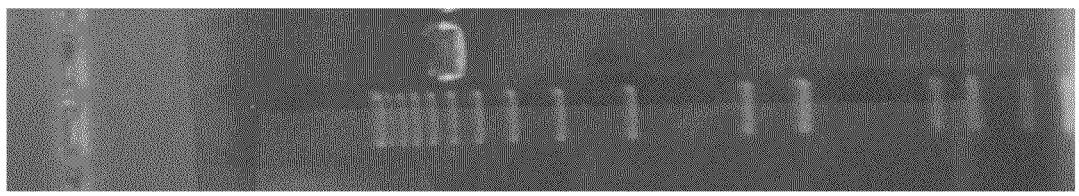
FIG. 3 shows the results of an EcoRI restriction digest of the Bi-cistronic FDH/PDHmod Plasmid.

One frozen vial of the E. coli host JM110 transformed with the bi-cistronic plasmid was thawed on ice and 100 µL inoculated to 20 mL of LB medium with 30 µg/mL kanamycin and incubated overnight at 30° C., 250 rpm. The cultures were transferred an additional 9 times to a fresh 20 mL volume of LB+30 µg/mL kanamycin and incubated 8-20 h at 30° C., 250 rpm. The plasmid DNA was isolated from the final 20 mL culture using a QIAGEN® midi plasmid kit. The plasmid was digested with EcoRI restriction enzyme and analyzed on an agarose gel (FIG. 3). A single band between the 6 and 7 Kb molecular weight markers was observed, the expected size for an intact linearized plasmid. No other bands are observed on the gel, indicating that the plasmid was genetically stable.

EXAMPLE 3

Fermentation of E. coli Transformant with Bi-Cistronic FDH/PDHmod Plasmid pBMS2000-FDH/PDHmod was transformed into E. coli JM110 and plasmid DNA was extracted and confirmed with the correct restriction enzyme digest pattern. JM110 (pBMS2000-FDH/PDHmod)+ was fermented in BMS medium (0.5% yeast extract, 0.22% glucose, 0.7% potassium phosphate (dibasic), 0.1% citric acid monohydrate, 0.17% ammonium sulfate, 0.003% ferrous sulfate heptahydrate, 0.23% magnesium sulfate heptahydrate, and 30 µg/mL kanamycin sulfate. For 4,000-L fermentor, the inoculum was prepared as follows: 1 mL of frozen JM110(pBMS2000-FDH/PDHmod)+ was thawed and added to a 600-L fermentor containing 400 L BMS medium with 30 µg/ml kanamycin. The fermentor was operated at 30° C., with an agitation of 150 rpm (revolution per minute), an aeration of 80 Lpm (liter per minute), and a head pressure of 7 psi for 21 hours. When $OD_{600}$ reached ~1.1, 75 L of culture was transferred to a 4,000-L fermentor containing 1,700 L BMS medium. The fermentor was initially grown at 30° C., with an agitation range of 105-150 rpm, an aeration range of 1,000-2,000 Lpm and a head pressure of 7 psi. Temperature and pressure remained constant during the run. A nutrient feed (10% yeast extract and 20% glucose) was started when the $CO_2$ was greater than 0.3% in the offgas. When $OD_{600}$ reached 20-25, the expression of both genes was induced by addition of filter-sterilized 1M isopropylthio-β-D galactopyranoside (IPTG) to a final concentration of 30 µM and the fermentation continued for a total of 48 hours.

EXAMPLE 4

Telescoped production of (αS)-α-[[(1,1-dimethylethoxy)carbonyl]amino]-3-hydroxytricyclo[3.3.1. 1$^{3,7}$] decane-1-acetic acid from 3-hydroxy-α-oxotricyclo-[3.3.1.1$^{3,7}$] decane-1-acetic acid through (αS)-α-amino-3-hydroxytricyclo[3.3.1.1$^{3,7}$] decane-1-acetic acid using an isolated (partially purified) PDH/FDH enzyme concentrate Isolation of PDH/FDH Enzyme Concentrate Fermentation broth (30 L) of Escherichia coli JM110 (pBMS2000-FDH/PDHmod)+ was obtained from a 4,000-L fermentation (prepared using the procedure similar to Example 3) and passed through a microfluidizer (Microfluidics model M-110Y, operating pressure 12,000-20,000 psi) (one pass) to release the activity from the cells keeping the temperature of the broth below 40° C. The PDH/FDH activity of microfluidized broth was 32 IU/mL for PDH and 8 IU/mL for FDH.

To clarify the whole broth, 4.5 kg of Celite was added to well-stirred broth. Then 0.201 L of 30% aqueous polyethyleneimine was added and mixed for 30 minutes. The mixture was then filtered using a filter press (Ertel Alsop model 8-ESSC-10) and 18 L of filtrate was obtained. The filter cake was washed with 12 L of water to bring the volume back to 30 L. The step yield was 97% activity recovery of PDH with an activity of 31 IU/mL and a FDH activity of 8 IU/mL.

The clarified broth was ultrafiltered through a 100,000 MWCO filter cassette (Millipore Pellicon 2 unit, polyethersulfone low protein binding cassette, 0.5 m² filter area). The circulation rate of the pump was 400 mL/min. The clarified filtrate was concentrated to 1.5 L and gave an enzyme concentrate with PDH titer of 567 IU/mL and FDH titer of 136 IU/mL. The permeate was assayed and no activity was found. The overall enzyme activity recovery in the concentrate was 84%.

Reductive Amination

3-Hydroxy-α-oxotricyclo-[3.3.1.1$^{3,7}$] decane-1-acetic acid (1.00 Kg; 4.46 mol) was added to a 20-L vessel followed by water (5 L). The mixture was stirred and the pH was adjusted to pH~8 with 10 N NaOH to give a solution. Darco KBB carbon (100 g) was added and the mixture was stirred for 5 minutes then filtered through a Buchner funnel with 5μ filter paper. The filter was washed with water (2×1 L) and the filtrates and washes were combined to give a clear solution.

With stirring, ammonium formate (0.562 Kg; 8.92 mol) was added and the pH was re-adjusted to ~7.5 with 10 N NaOH. Nicotinamide adenine dinucleotide (2.65 g) and dithiothreitol (1.54 g) were added. When the solids had dissolved, a PDH/FDH enzyme concentrate was added (1.03 L; 500,000 IU of PDH). The pH was re-adjusted to ~8.0 with 10 N NaOH at ambient temperature.

The mixture was then warmed to ~40° C. and diluted to a total volume of 10 L with water. The pH was maintained at 7.7-8.3 while stirring over 42 hours. The resulting solution contained 0.955 Kg (95.1%) of the product (αS)-α-amino-3-hydroxytricyclo[3.3.1.1$^{3,7}$] decane-1-acetic acid.

BOC-Protection

Di-tert-butyl dicarbonate (1.022 Kg; 4.68 mol) was added to a portion of the solution of (αS)-α-amino-3-hydroxytricyclo[3.3.1.1$^{3,7}$] decane-1-acetic acid (477.5 g; 2.12 mol). This mixture was stirred at ambient temperature, with pH adjusted to and maintained at 10 with a pH stat titrator using 10 N NaOH. The reaction was complete 4 hours after Boc$_2$O addition when there was less than 1.0% starting material remaining The pH of the mixture was adjusted to ~8 with 35% H$_2$SO$_4$ and i-PrOAc (5.0 L) was added to the mixture. The pH of the mixture was then adjusted to 2.0 with 35% H$_2$SO$_4$ and maintained at this pH for 5-10 minutes. Dicalite (250 g) was added; the mixture was stirred for ~10 minutes, and then filtered through a pad of Dicalite (250 g) on filter paper in a Buchner funnel. The Dicalite pad was further washed with 2.5 L i-PrOAc.

The filtrate was adjusted to pH 8 with 10 N NaOH. After settling for 1 hr, the organic layer including interface was discarded. To the aqueous layer, i-PrOAc (7.5 L) was added. The mixture was acidified with 35% H$_2$SO$_4$ to pH~2, and then heated to and maintained at ~40° C. for 4 hours with mild stirring. The layers were separated and the organic extract was saved. The aqueous layer with interface was extracted with i-PrOAc (3.75 L) and the layers were again separated after 2 hours at 40° C. The aqueous layer with interface was extracted again with i-PrOAc (3.75 L) and the layers were separated after 2 hours at 40° C.

The combined organic extracts (~15 L) were concentrated by distillation to ~4.5 L. To this solution, heptane (~10 L) was then added over 10-15 minutes while the temperature was maintained at ~82-89° C. The reactor jacket temperature was set to 70° C. and maintained at this temperature for 1 hour. Crystallization occurred shortly after cooling. The reactor jacket temperature was then set at 40° C. and maintained at this temperature for 30 minutes.

The suspension was cooled down to ambient temperature, and then further cooled to 0-5° C. After one hour of stirring at 0-5° C., the product was filtered. The product was washed with heptane (2.5 L), then dried in vacuo at 40° C. to give 607.0 g (88% yield) of (αS)-α-[[(1,1-dimethylethoxy)carbonyl]amino]-3-hydroxytricyclo[3.3.1.1$^{3,7}$] decane-1-acetic acid.

It should be understood that the foregoing disclosure emphasizes certain specific embodiments and that all modifications or alternatives equivalent thereto are within the spirit and scope of the invention as set forth in the appended claims.

What is claimed is:

1. An isolated nucleic acid molecule encoding a polypeptide having formate dehydrogenase activity and a polypeptide having phenylalanine dehydrogenase activity comprising:
   (a) an isolated nucleic acid sequence comprising a nucleotide sequence that is 95% identical to SEQ ID NO: 1; or
   (b) a sequence encoding the polypeptide of SEQ ID NO:4 and the polypeptide of SEQ ID NO: 5.

2. An isolated nucleic acid molecule comprising the nucleotide sequence of SEQ ID NO: 1.

3. The isolated nucleic acid molecule of claim 1, wherein the sequence encoding the polypeptide of SEQ ID NO: 4 and the polypeptide of SEQ ID NO: 5 further comprises a single promoter region.

4. An isolated nucleic acid molecule comprising a sequence that hybridizes to the complement of the nucleotide sequence of SEQ ID NO: 1 at 42° C. in a hybridization buffer comprising 50% formamide, 5×SSC (0.75 M NaCl, 0.075 M sodium citrate), 50 mM sodium phosphate (pH 6.8), 0.1% sodium pyrophosphate, 0.1% SDS, and 10% dextran sulfate, and then at 42° C. in a hybridization wash buffer comprising 0.2×SSC and 0.1% SDS,
   wherein the nucleic acid molecule encodes a polypeptide having formate dehydrogenase activity and a polypeptide having phenylalanine dehydrogenase activity.

5. An isolated nucleic acid molecule comprising the nucleotide sequence of SEQ ID NO: 2.

6. A plasmid comprising the nucleic acid molecule of claim 2.

7. An isolated host cell comprising the plasmid of claim 6.

8. The host cell of claim 7 that is a prokaryotic cell.

9. A method for producing (αS)-α-[[(1,1-dimethylethyoxy)carboxyl]-amino]-3-hydroxytricyclo[3.3.1.1$^{3,7}$]decane-1-acetic acid (Formula I):

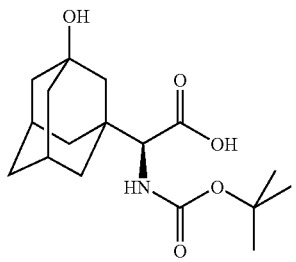

(I)

wherein the method comprises:
   (a) culturing the host cell of claim 8 under suitable conditions to express the polypeptides encoded by the nucleic acid molecule of SEQ ID NO: 1;
   (b) partially purifying an enzyme concentrate comprising the polypeptides; and
   (c) contacting the culture isolate with an amount of 3-hydroxy-α-oxotricyclo-[3.3.1.1$^{3,7}$]decane-1-acetic acid (Formula II):

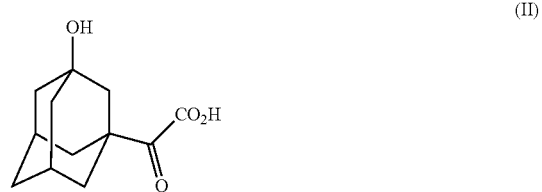

(II)

under conditions that allow for production of (αS)-α-amino-3-hydroxytricyclo[3.3.1.1$^{3,7}$]decane-1-acetic acid (Formula III):

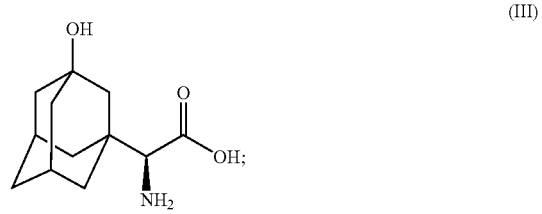

(III)

(d) contacting the (αS)-α-amino-3-hydroxytricyclo[3.3.1.1$^{3,7}$]decane-1-acetic acid with an amount of di-tent-butyl dicarbonate under conditions that allow for production of (αS)-α-[[(1,1-dimethylethyoxy)carboxyl]-amino]-3-hydroxytricyclo[3.3.1.1$^{3,7}$]decane-1-acetic acid.

* * * * *

UNITED STATES PATENT AND TRADEMARK OFFICE
CERTIFICATE OF CORRECTION

PATENT NO. : 8,158,394 B2
APPLICATION NO. : 12/756700
DATED : April 17, 2012
INVENTOR(S) : Jonathan Basch et al.

It is certified that error appears in the above-identified patent and that said Letters Patent is hereby corrected as shown below:

Title Page (Other Publications):
    Column 2, line 14, Delete "Mukalyama" and insert -- Mukaiyama --, therefor.

In the Claims:
    Column 38, line 53, claim 9, after

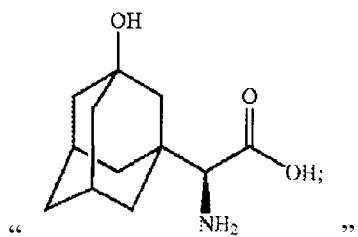

insert -- and --.

Column 38, line 59, delete "tent" and insert -- tert --, therefor.

Signed and Sealed this
Thirtieth Day of April, 2013

Teresa Stanek Rea
*Acting Director of the United States Patent and Trademark Office*